United States Patent
Richardson et al.

(10) Patent No.: US 7,754,075 B2
(45) Date of Patent: Jul. 13, 2010

(54) BACKFLOW PREVENTION FOR HIGH PRESSURE GRADIENT SYSTEMS

(75) Inventors: Hal Richardson, Westborough, MA (US); Richard W. Andrews, Rehoboth, MA (US)

(73) Assignee: Waters Technologies Corporation, Milford, MA (US)

( * ) Notice: Subject to any disclaimer, the term of this patent is extended or adjusted under 35 U.S.C. 154(b) by 189 days.

(21) Appl. No.: 12/113,253

(22) Filed: May 1, 2008

(65) Prior Publication Data

US 2008/0251141 A1    Oct. 16, 2008

Related U.S. Application Data

(62) Division of application No. 10/911,111, filed on Aug. 4, 2004, now Pat. No. 7,396,469, which is a division of application No. 10/314,725, filed on Dec. 9, 2002, now Pat. No. 6,780,315.

(51) Int. Cl.
*B01D 15/08* (2006.01)

(52) U.S. Cl. .......... 210/198.2; 210/656; 210/101; 137/606; 366/162.4; 366/162.5

(58) Field of Classification Search ............. 210/656, 210/659, 101, 137, 143, 198.2; 417/3, 4, 417/5, 6, 7, 8; 366/162.4, 162.5, 182.4; 137/602, 137/605, 606

See application file for complete search history.

(56) References Cited

U.S. PATENT DOCUMENTS

| | | | |
|---|---|---|---|
| 4,045,343 A * | 8/1977 | Achener et al. ............. 210/101 |
| 4,233,265 A * | 11/1980 | Gasper ..................... 422/135 |
| 4,506,987 A * | 3/1985 | Daughton et al. ......... 366/160.3 |
| 4,690,165 A * | 9/1987 | Leytes et al. ................ 137/112 |
| 6,679,274 B2 * | 1/2004 | Gruszczynski et al. ... 134/22.12 |
| 6,780,315 B2 * | 8/2004 | Richardson et al. ...... 210/198.2 |
| 7,396,469 B2 * | 7/2008 | Andrews et al. ............ 210/656 |

* cited by examiner

*Primary Examiner*—Ernest G Therkorn
(74) *Attorney, Agent, or Firm*—Anthony J. Janiuk; Siqun Huang

(57) ABSTRACT

Gradient performance with high pressure gradient solvent delivery system is optimized by approximation of infinite stroke volume of high pressure pumps by the addition of pulse dampening with backflow prevention to each high pressure pump. The backflow prevention adds sufficient minimum flow resistance, thereby enhancing the performance of the pulse dampening over a wider range of flow rates resulting in consistent gradient performance.

4 Claims, 8 Drawing Sheets

BACKFLOW PREVENTION FOR HIGH PRESSURE GRADIENT SYSTEMS

CROSS REFERENCE TO RELATED APPLICATIONS

This application is a division of U.S. application Ser. No. 10/911,111, filed Aug. 4, 2004, which is a divisional of U.S. application Ser. No. 10/314,725, filed Dec. 9, 2002, now U.S. Pat. No. 6,780,315, the entire contents of which are incorporated herein by reference.

FIELD OF THE INVENTION

Background of the Invention

High-pressure liquid chromatography (HPLC) solvent delivery systems are used to source single-component liquids or mixtures of liquids (both known as "mobile phase") at pressures which can range from substantially atmospheric pressure to pressures on the order of ten thousand pounds per square inch. These pressures are required to force the mobile phase through the fluid passageways of a stationary phase support, where separation of dissolved analytes can occur. The stationary phase support may comprise a packed bed of particles, a membrane or collection of membranes, a porous monolithic bed, or an open tube. Often, analytical conditions require the mobile phase composition to change over the course of the analysis (this mode being termed "gradient elution"). In gradient elution, the viscosity of the mobile phase may change and the pressure necessary to maintain the required volumetric flow rate will change accordingly.

In liquid chromatography, the choice of an appropriate separation strategy (including hardware, software, and chemistry) results in the separation of an injected sample mixture into its components, which elute from the column in reasonably distinct zones or "bands". As these bands pass through a detector, their presence can be monitored and a detector output (usually in the form of an electrical signal) can be produced. The pattern of analyte concentration within the eluting bands, which can be represented by means of a time-varying electrical signal, gives rise to the nomenclature of a "chromatographic peak". Peaks may be characterized with respect to their "retention time", which is the time at which the center of the band transits the detector, relative to the time of injection (i.e. time-of-injection is equal to zero). In many applications, the retention time of a peak is used to infer the identity of the eluting analyte, based upon related analyses with standards and calibrants. The retention time for a peak is strongly influenced by the mobile phase composition, and by the accumulated volume of mobile phase which has passed over the stationary phase.

The utility of chromatography relies heavily on run-to-run reproducibility, such that standards or calibrants can be analyzed in one set of runs, followed by test samples or unknowns, followed by more standards, in order that confidence can be had in the resulting data. Known pumping systems exhibit some non-ideal characteristics which result in diminished separation performance and diminished run-to-run reproducibility. Among the non-ideal pump characteristics exhibited in own pumping systems are, generally, fluctuations in solvent composition and/or fluctuations in volumetric flow rate.

Volumetric flow fluctuations present in known HPLC pumping systems disadvantageously cause retention time(s) to vary for a given analyte. That is, the amount of time that an analyte is retained in the stationary phase fluctuates undesirably as a function of the undesirable volumetric flow fluctuations. This creates difficulties in inferring the identity of a sample from the retention behavior of the components. Volumetric flow fluctuations from individual pumps can result in fluctuations in solvent composition when the output of multiple pumps is summed to provide a solvent composition.

Fluctuations in solvent composition present in known HPLC pumping systems can disadvantageously result in interactions with the system's analyte detector and produce perturbations which are detected as if they arose from the presence of a sample. In effect, an interference signal is generated. This interference signal is summed with the actual signal attributable to the analyte, producing errors when the quantity of an unknown sample is calculated from the area of the eluting sample peak.

The prior art is replete with techniques and instrument implementations aimed at controlling solvent delivery and minimizing perturbations in the output of delivery systems for analytical instrumentation. Myriad pump configurations are known which deliver fluid at high pressure for use in applications such as liquid chromatography. Known pumps, such as one disclosed in U.S. Pat. No. 4,883,409 ("the '409 patent") incorporate at least one plunger or piston which is reciprocated within a pump chamber into which fluid is introduced. A controlled reciprocation frequency and stroke length of the plunger within the pump chamber determines the flow rate of fluid output from the pump. However, the assembly for driving the plunger is an elaborate combination of elements that can introduce undesirable motion in the plunger as it is driven, which motion makes it difficult to precisely control the solvent delivery system output and results in what is termed "noise" or detectable perturbations in a chromatographic baseline. Much of this noise does not result from random statistical variation in the system, rather much of it is a function of a mechanical "signature" of the pump. Mechanical signature is correlated to mechanically related phenomena such as anomalies in hall and screw drives, gears, and/or other components used in the pump to effect the linear motion that drives the piston(s), or it is related to higher level processes or physical phenomena such as the onset or completion of solvent compression, or the onset of solvent delivery from the pump chamber.

Typical systems known for delivery of liquids in liquid chromatography applications, such as disclosed in the '409 patent and further in U.S. Pat. No. 5,393,434, implement dual piston pumps having two interconnected pump heads each with a reciprocating plunger. The plungers are driven with a predetermined phase difference in order to minimize output flow variations. Piston stroke length and stroke frequency can be independently adjusted when the pistons are independently, synchronously driven. Precompression can be effected in each pump cylinder in any given pump cycle to compensate for varying fluid compressibilities in an effort to maintain a substantially constant system pressure and output flow rate.

There are two widely used means to create gradient HPLC pumps. The solvents can be blended on the intake side of the pump. This is known in the art as low pressure gradient mixing. The alternative is the use of so-called high pressure gradient systems in which each individual solvent is delivered by a separate pump.

The fundamental scalar of all forms of gradient chromatography is the void volume of the separation column. The void volume of an HPLC column is the sum of the inter and intra particle volumes of the column that are filled with mobile phase. The void volume is the minimum volume required to elute an unretained solute. The gradient delay volume is the volume of the mobile phase delivered from the time the gradient is initiated to when the change in composition first arrives at the column. The delay volume is the volumetric overhead of the gradient solvent delivery system; it adds to the time required to complete the separation and to prepare the column for the next injection. The delay volume should be minimized and ideally should be no more than two times larger than the void volume of the column.

When two or more high pressure pumps are combined to form a gradient solvent delivery system, their outputs are combined with the resulting possibility that there can be fluidic cross talk between the high pressure pumps during their individual piston crossovers. One prior approach to avoid fluidic cross talk has been the use of pulse dampeners within the gradient solvent delivery system as shown in FIG. 1.

When individual pulse dampeners are placed up-stream from where output of the solvents meet and the total flow is small relative to the volume of the pulse dampeners, there will be significant crosstalk between the pumps since the two pumps are not synchronous in their respective piston crossovers. This crosstalk occurs because the fluid contained in the off line pulse dampener can be compressed making it the low impedance path for the on-line pump. As such, this up-stream placement of the pulse dampeners results in a compromised flow rate and composition. The result of this fluidic crosstalk is shown in FIG. 2, which plots the delivery of a gradient marker from a solvent delivery system configured as shown in FIG. 1 at a low flow rate. As shown in FIG. 2, no gradient deliveries are identical and none correspond to the programmed gradient. This results in unsatisfactory and unpredictable separations which cannot be reproduced.

In an alternative prior art approach, a capillary restrictor is used to generate backpressure to energize the pulse dampeners. A capillary of fixed length and internal diameter provides sufficient backpressure to restrict, but unfortunately not prevent backflow, over narrow ranges of flow rates.

A further approach to the use of pulse dampeners is to position a pulse dampener downstream from the common mixing tee. While this approach is useful in gradient systems having large volumes, smaller scale volumes are problematic. The positioning of a pulse dampener after the common mixing tee greatly increases the delay volume within the gradient systems. Pulse dampeners are scaled to a specific and limited flow rate range as they typically combine resistance to flow and a captive capacitive volume of the mobile phase. The requirements of effective pulse dampening and minimizing delay volume will conflict as the scale of the HPLC system with respect to column volume and volumetric flow rate is reduced.

SUMMARY OF THE INVENTION

The present invention provides an improved method and apparatus for improving the compositional accuracy of high pressure gradient pumps for HPLC by approximation of infinite stroke volume with backflow prevented pulse dampening. The backflow prevention, according to the invention, adds sufficient minimum flow resistance thereby enhancing the performance of the pulse dampening over a wider range of flow rates resulting in consistent gradient performance.

According to the invention, pulse dampeners in conjunction with back flow preventors, which may be embodied as check valves or in-line back-pressure regulators, ensure that the stored mobile phase is compressed during the delivery cycle. When a backflow preventor with a fixed minimum flow resistance is used, the effectiveness of the pulse dampener becomes substantially independent of the flow rate. The use of backflow preventors within the gradient system ensures that the stored mobile phase is compressed and has mechanical energy to return to the system at piston crossover.

The backflow preventors further ensure that the outlet check valves of the respective pump heads will experience sufficient backpressure allowing for their proper functioning. This sufficient backpressure is particularly helpful in systems having low flow rates when the backpressure generated by the column and tubing is limited. Additionally, backpressure allows the primary check valves of individual pumps to operate more consistently as the resulting backpressure ensures proper seating of the outlet check valve on the pump head that is off line.

The proper placement of a backflow preventor according to the invention reduces fluidic cross talk, optimizes the performance of in-line pulse dampers and enhances the performance of the high pressure pumps as shown in FIG. 3., which plots the delivery of a gradient marker from a solvent delivery system configured with backflow prevention according to the invention. As depicted in FIG. 3, the gradient deliveries are identical and correspond to the programmed gradient.

Advantageously, individual pumps deliver smooth flow by the addition of suitable pulse dampeners with the further use of backflow preventors that prevent fluidic cross talk between the two mobile phases. Because a pulse dampener is the fluidic equivalent of a low pass filter, when a small stroke volume is combined with a pulse dampener, the crossover perturbations occur at frequencies that are strongly attenuated. The differences between individual pump heads are effectively averaged by the use of pulse dampeners. Thus, the use of small stoke volumes with efficient pulse dampening provide for uniform blending of solvents in high pressure gradient systems.

In an alternative illustrative embodiment a capillary restrictor is used to generate backpressure to energize the pulse dampener. A capillary of fixed length and internal diameter provides sufficient backpressure over a certain range of flow rates. The use of a capillary restrictor in series with a check valve can be used for systems having consistent flow rates.

In a further alternative illustrative embodiment the check valves are incorporated into a mixing tee. This incorporation decreases the volume of the mobile phase within the gradient system and therefore decreases the delay volume of the gradient system.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION OF THE INVENTION

The present disclosure will he described in detail with respect to chromatographic applications with the understanding that embodiments of the present invention are directed to industrial and process control applications as well.

Figure 1:
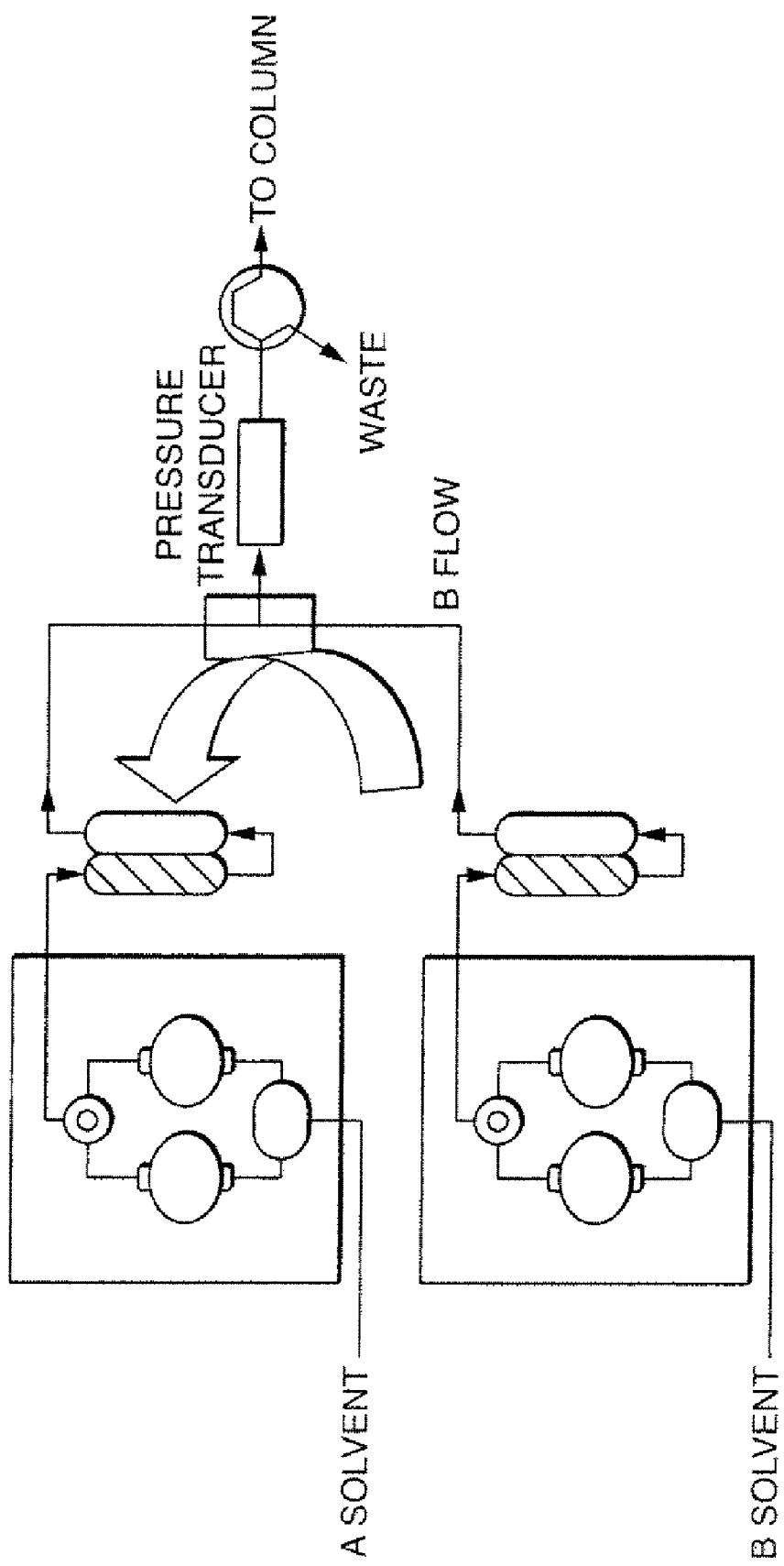
FIG. 1 is a schematic of a standard high pressure gradient pump (prior art)
Figure 2:
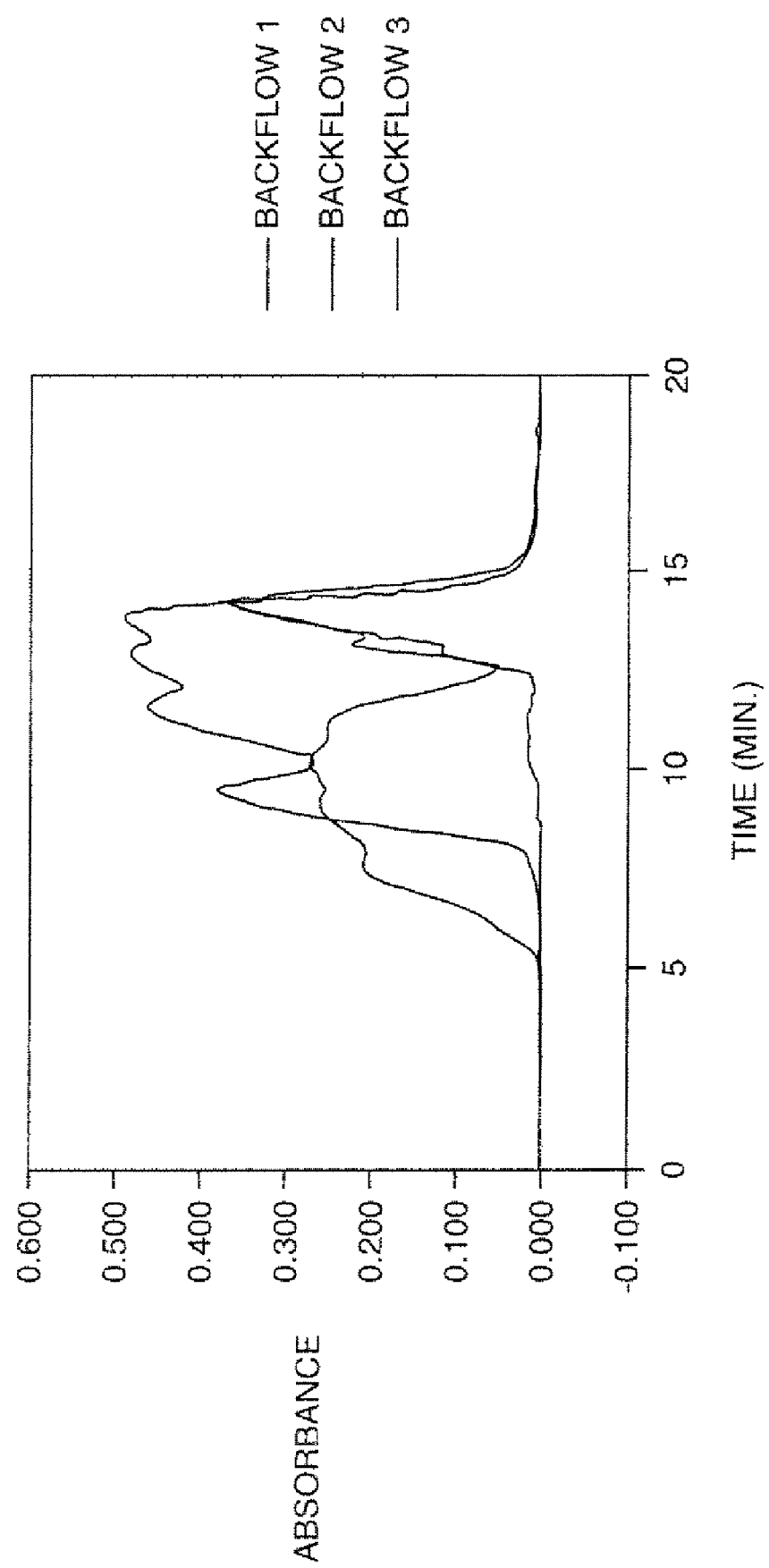
FIG. 2 demonstrates problems with fluidic crosstalk in high pressure gradient systems (prior art)
Figure 3:
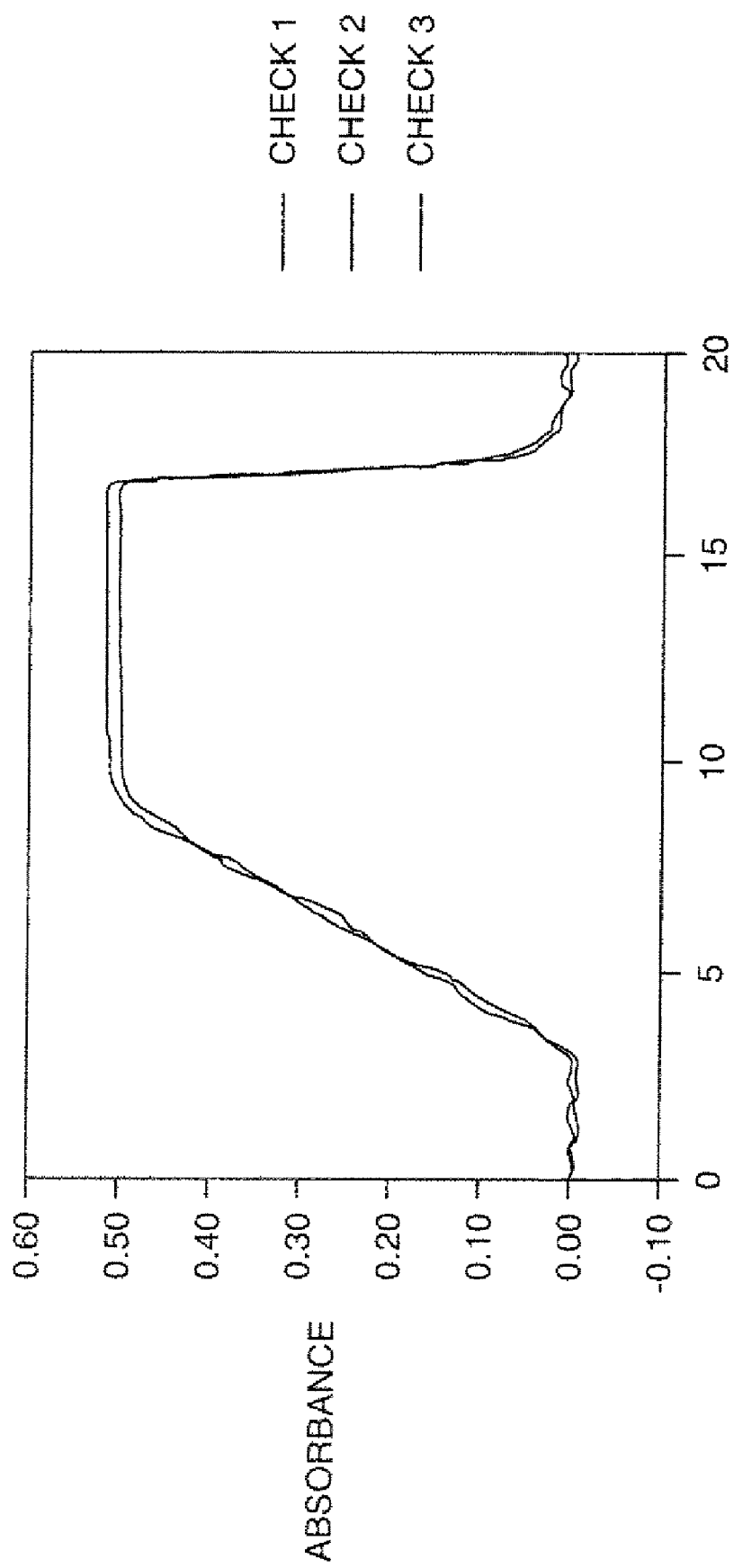
FIG. 3 illustrates the effect of pump crossover on solvent composition without backflow prevention (prior art)
Figure 4:
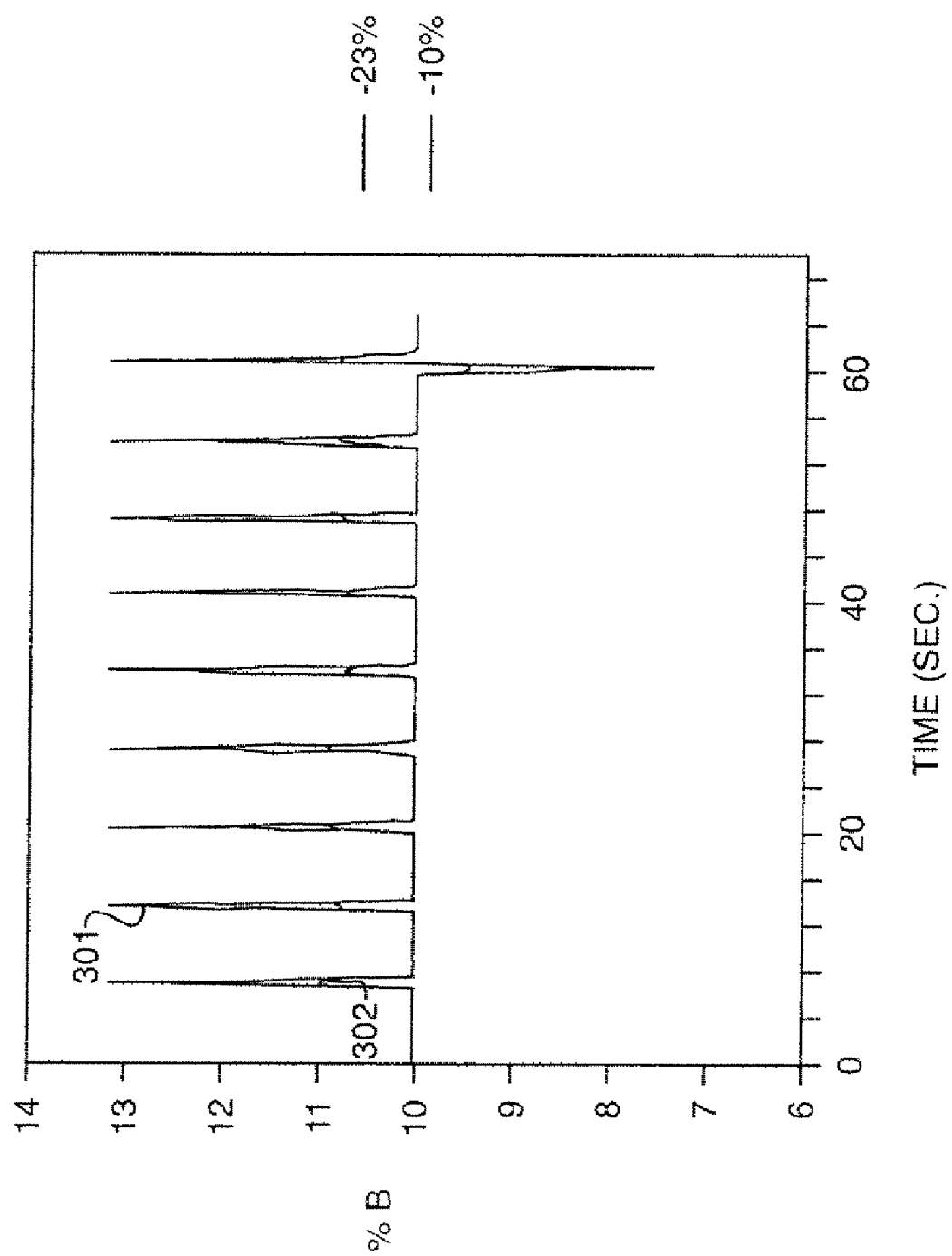
FIG. 4 demonstrates the use of pulse dampers with the addition of in-line check valves according to the invention.

As shown in FIG. 4 the effect of pump crossover on solvent composition is illustrated. Within this illustration, the total flow is 1 mL/min. A first pump delivers ninety percent of the flow or approximately 900 µL/min. A second pump delivers ten percent of the flow or approximately 100 µL/min. The stroke volume is approximately 100 µL for both pumps. There are nine crossovers of the first pump to one crossover of the second pump to provide the desired composition. When the first pump crosses over there is a deficit in the first solvent of about 23 percent in flow rate and the composition is momentarily enriched in the second solvent. This deficit is illustrated by a first curve 301. A second curve 302 shows the effect of reducing the magnitude of the flow rate deficit from about 23 percent loss of flow at crossover to 10 percent loss of flow by the use of limited pulse dampening. The compositional perturbations or "noise" is reduced from about ±3 percent of the second solvent delivered to about ±1 percent of the second solvent delivered. Further pulse dampening according to the invention would further reduce the compositional noise.

The effect of this compositional noise on the retention times of analyte peaks is strongly dependent upon the degree of retention of the analyte and is expressed in its k-prime (k') value which is the number of column volumes required to elute the analyte from the column. The k' value is computed from the following formula:

$$k'=(V_r-V_o)/V_o \qquad \text{(Formula 1)}$$

where $V_r$=retention volume and $V_o$=column void volume.

When k' is small, variations in mobile phase composition have little effect on retention volume, however when k' is large small variations in mobile phase composition have a large effect on retention volume since k' is exponentially proportional to the percent of the second solvent delivered.

Figure 5:
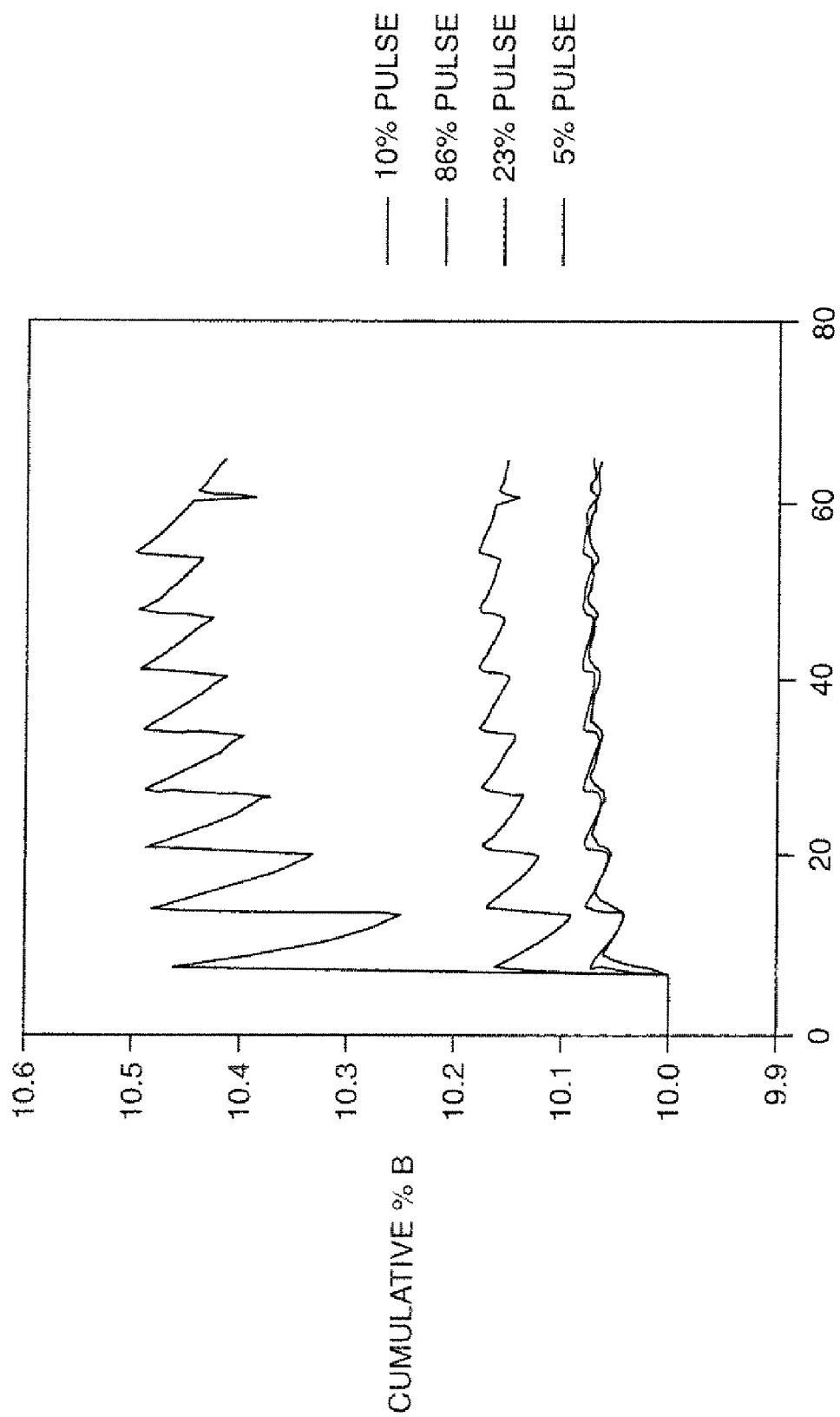
FIG. 5 illustrates the cumulative effect of pump crossover on solvent composition (prior art)

The cumulative effect of pump crossovers on the percent of the second solvent delivered is illustrated in FIG. 5. The cumulative error in the percent of the second solvent is strongly coupled to the magnitude of the gradient pulse. The resulting variance in retention times will be strongly coupled with the degree of pulsation and the mixing requirement ensuring a more uniform composition is directly coupled to the instantaneous and the cumulative errors in the percent of the second solvent. When the pulsations are reduced according to the invention the composition becomes inherently more uniform and requires a smaller volume to ensure its uniformity.

Figure 6:
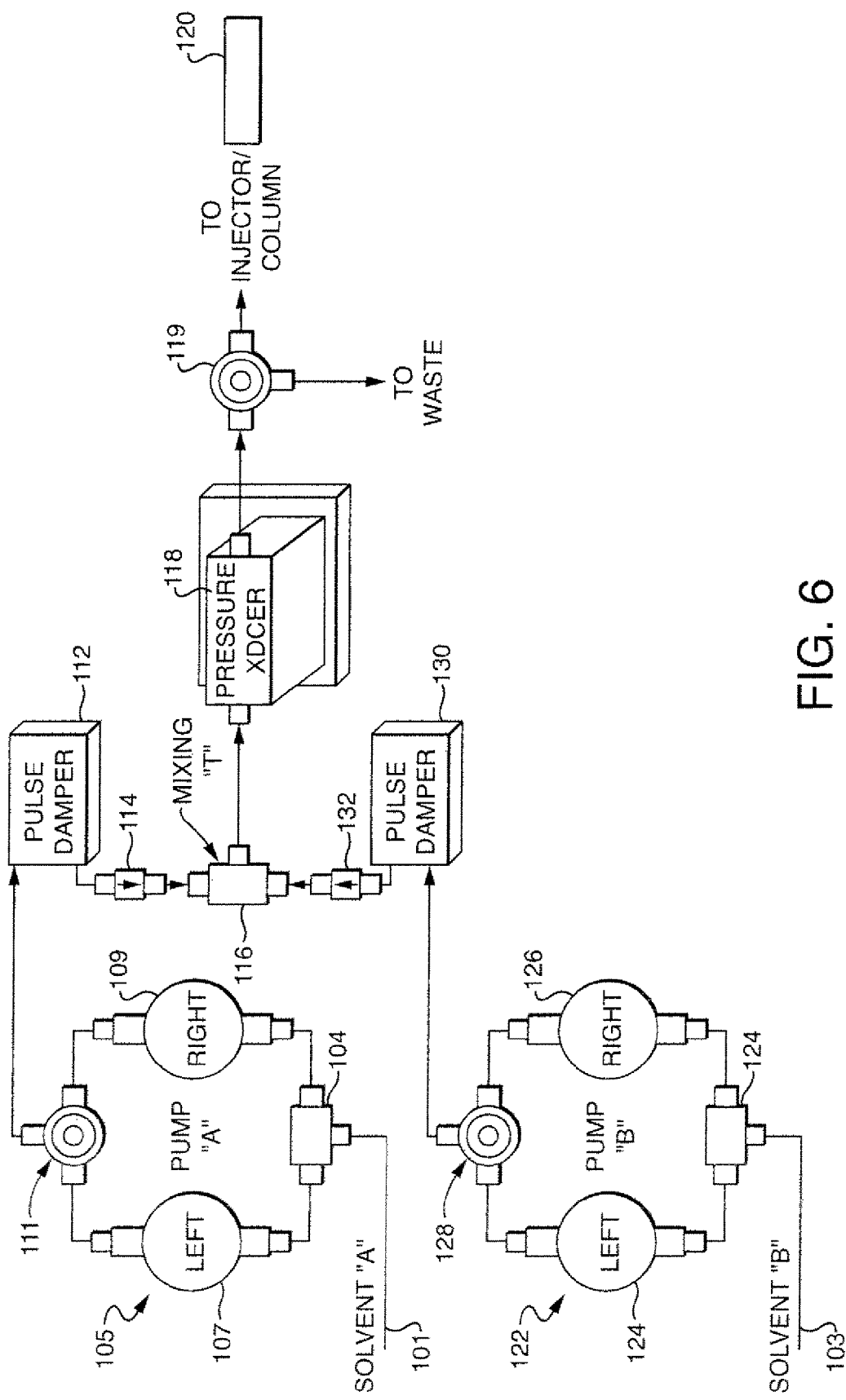
FIG. 6 is a schematic of a high pressure gradient pumping system according to the invention.

Turning to FIG. 6, an illustrative embodiment of the instant invention is a high pressure gradient system in which each individual solvent is delivered by a separate pump. This illustrative embodiment has a first solvent delivery line 101 and a second solvent delivery line 103. A first solvent is delivered to a first pump 105 within the first solvent delivery line 101 via a fluidic tee 104. The first pump 105 has a first piston 107 and a second piston 109. In this illustrative embodiment the first pump 105 is a Waters model HPLC pump 515, made by Waters Corporation of Milford Mass., which is a fluidic pump having a fixed stroke length. It is contemplated within the scope of this invention that other pumps known in the art may be used.

The first solvent is delivered via the first pump 105 to a prime valve 111, such as Waters P/N WAT 207085, Waters Corporation, Milford, Mass., which also acts as a fluidic tee receiving the output from the first piston 107 and the second piston 109. The first solvent is delivered to a first pulse dampener 112. The first pulse dampener 112, which in this illustrative embodiment is a Waters High Pressure Filter, P/N WAT207072, Waters Corporation, Milford, Mass., is a fluidic low pass filter that minimizes flow rate perturbation within the first solvent delivery line. It is contemplated within the scope of this invention that other pulse dampeners known in the art may be used.

The first solvent is pumped through the first pulse dampener 112 and is delivered to a first backflow preventor 114. The first backflow preventor 114, which in this illustrative embodiment is an Upchurch Model U-609, Upchurch Scientific, Oak Harbor, Wash., has a known resistance to flow forces that causes a load onto the first pulse dampener 112 ensuring consistent operation of the first pulse dampener 112. This resistance to flow can range from about 0 to 2,000 psi, and in this first illustrative embodiment the resistance is approximately 250 psi.

The first backflow preventor 114 is in fluid communication with a common mixing tee 116 that directs the first solvent through a pressure transducer 118 and into a vent valve 119, such as Rheodyne 7033, Rheodyne, LP., Rohnert Park, Calif. The vent valve 119 directs the first solvent to an injector and a chromatography column 120.

A second solvent is delivered to a second pump 122 within the second solvent delivery line 103 via a second fluidic tee 124. The second pump 122 has a first piston 124 and a second piston 126. In this illustrative embodiment the second pump 122 is a Waters model 515 HPLC pump, Waters Corporation Milford Mass., which is a fluidic pump having a fixed stroke length. It is contemplated within the scope of this invention that other pumps known in the art may be used.

The second solvent is delivered via the second pump 122 to second prime valve 128, such as Waters P/N WAT 207085, Waters Corporation, Milford, Mass., which also acts as a fluidic tee receiving the output from the first piston 124 and the second piston 126. The second solvent is delivered to a second pulse dampener 130. The second pulse dampener 130 provides a fluidic low pass filter that minimizes flow rate perturbations within the second solvent delivery line. The second solvent is pumped to a second backflow preventor 132. The second backflow preventor 132 has a known resistance to flow forces that causes a pressure load onto the second pulse dampener 130 ensuring consistent operation of the second pulse dampener 130. This resistance to flow can range from 0 to 2000 psi, and in this first illustrative embodiment the resistance is approximately 250 psi.

The second backflow preventor 132 is in fluid communication with the common mixing tee 116 that directs the first solvent through the pressure transducer 118 and into the vent valve 119 and the second solvent 102 through the pressure transducer 118 and into the vent valve 119. The vent valve 119, such as a Rheodyne 7033, Rheodyne, LP., Rohnert Park, Calif., directs the first solvent 101 and the second solvent 102 to the chromatography column 120.

Figure 7:
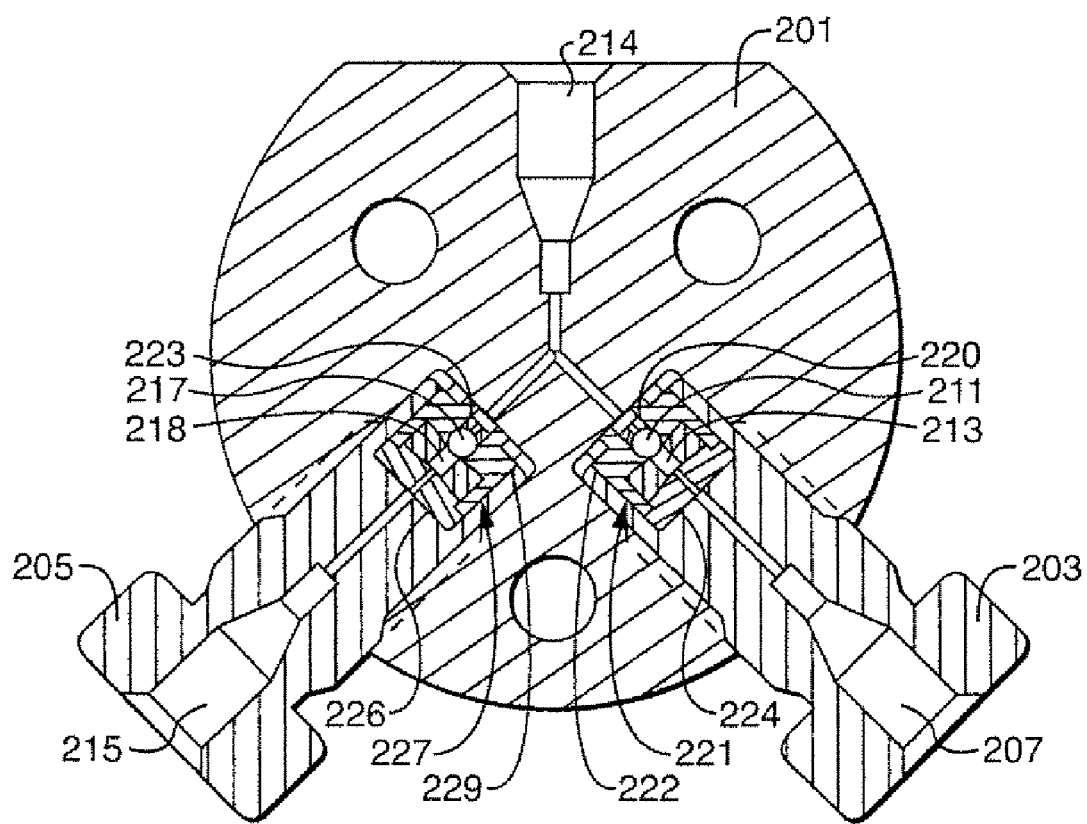
FIG. 7 is a schematic of a mixing tee having integrated check valves.

In an alternative embodiment of the invention the first backflow preventor and the second backflow preventor are incorporated into the structure of the mixing tee to minimize system volume. As illustrated in FIG. 7 the common mixing tee 201 has a first backflow preventor 203 and a second backflow preventor 205 incorporated into the structure of the mixing tee 201. The mixing tee 201 has a first inlet port 207 in which the first backflow preventor 203 is incorporated, a second inlet port 215 in which the second backflow preventor 205 is incorporated and an outlet port 214 in which fluid flow from the first inlet port 207 and the second inlet port 215 are directed.

The first backflow preventor 203 has a first ball bearing 211 housed within a first check valve body 220. The first ball bearing 211 is seated in a first check valve seat 213. The first ball bearing 211 is fabricated from materials that are inert to system solvents such as sapphire and ceramic or the like. The first ball bearing 211 is encased in a first check valve cartridge housing component 221 in a manner allowing only forward fluid flow. The first check valve cartridge housing component 221 is comprised of a top part 222 and a base part 224, which forms the first check valve seat 213.

The second backflow preventor 205 has a second ball bearing 217 housed within a second check valve body 223. The second ball bearing 217 is seated in a second check valve seat 218. The second ball bearing 217 is fabricated from materials that are inert to system solvents such as sapphire and ceramic or the like. The second ball bearing 217 is encased in a second check valve cartridge housing component 227 in a manner only allowing forward fluid flow. The second check valve cartridge housing component 227 is comprised of a top part 229 and a base part 226 which forms the second check valve seat 218.

Figure 8:
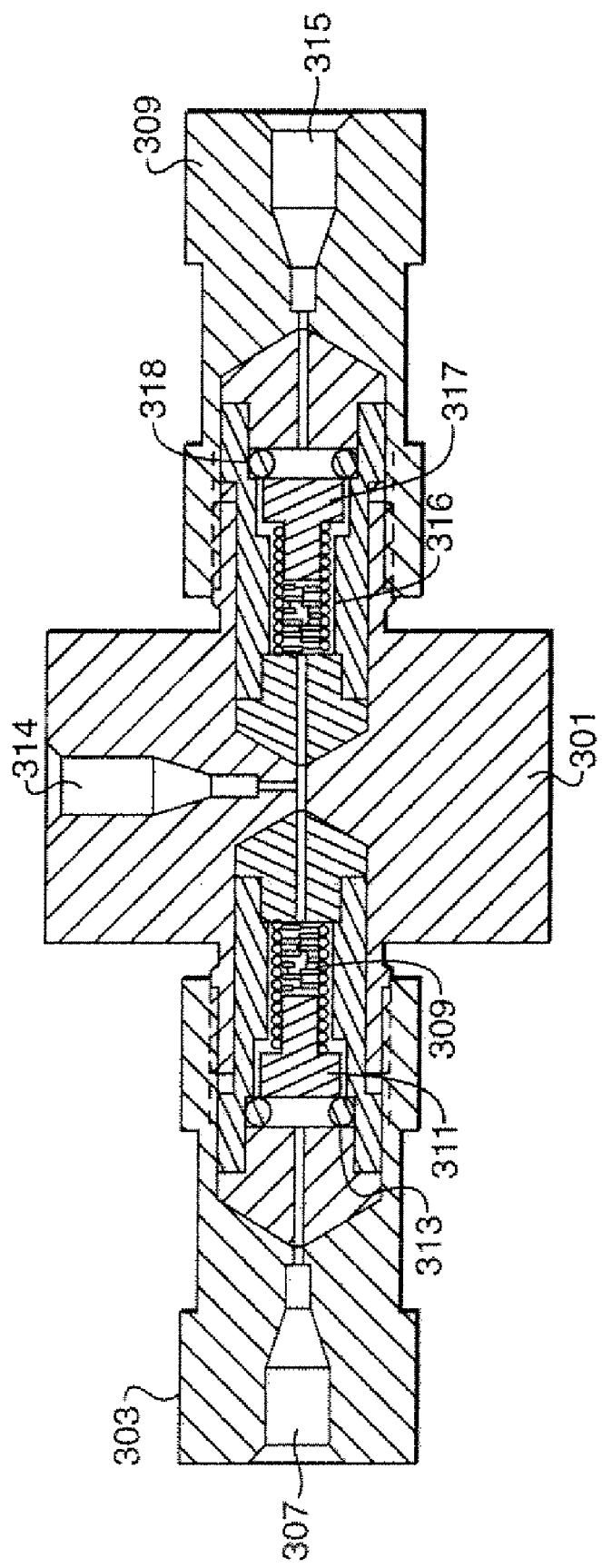
FIG. 8 is a schematic of a mixing tee having integrated check valves and backpressure regulators.

In a further alternative embodiment of the invention the first backflow preventor and the second backflow preventor are incorporated into the structure of the mixing tee to minimize system volume. As illustrated in FIG. 8 the common mixing tee 301 has a first backflow preventor 303 and a second backflow preventor 305 incorporated into the structure of the mixing tee 301. The mixing tee 301 has a first inlet port 307 in which the first backflow preventor 303 is incorporated, a second inlet port 315 in which the second backflow preventor 305 is incorporated and an outlet port 314 in which fluid flow from the first inlet port 307 and the second inlet port 315 are directed.

The first backflow preventor 303 has a coil spring 309 that applies pressure to a first actuator 311. The first actuator 311 is seated into a first valve opening 313. The selected coil spring 309 provides a certain resistance to flow by exerting pressure against the first actuator thereby sealing the first valve opening 313 until the resistance to flow is exceeded.

The second backflow preventor 305 has a coil spring 316 that applies pressure to a second actuator 317. The second actuator 317 is seated into a second valve opening 318. Again, the selected coil spring 316 provides a certain resistance to flow by exerting pressure against the second actuator 317 thereby sealing the second valve opening 318 until the resistance to flow is exceeded.

In a further alternative embodiment the pulse dampeners within the fluidic solvent delivery lines are configured from a section of capillary tubing whose length and diameter are optimized to provide the necessary volume within the capillary tubing to minimize flow rate perturbations.

Although the chromatography pumping system described in the illustrative embodiment herein is configured to accommodate two separate solvent sources it should be appreciated that multiple or single solvent delivery systems as are known in the art can be implemented.

Although the chromatography pumping system described in the illustrative embodiment herein is configured having traditional actuator and spring backflow preventors it should be appreciated that other backflow preventors that are known in the art can be used.

The foregoing describes specific embodiments of the inventive method and apparatus. The present disclosure is not limited in scope by the illustrative embodiments described, which are intended as specific illustrations of individual aspects of the disclosure. Equivalent methods and components are within the scope of the disclosure. Indeed, the instant disclosure permits various and further modifications to the illustrative embodiments, which will become apparent to those skilled in the art. Such modifications are intended to fall within the scope of the appended claims.

What is claimed is:

1. A high pressure liquid chromatography apparatus comprising: a mixing tee having an outlet port, a first inlet port and a second inlet port; and a backflow preventer incorporated within said first and second inlet port said backflow preventer having a coil spring and an actuator seated within a valve seat wherein said coil spring exerts a selected pressure upon said actuator.

2. The high pressure liquid chromatography apparatus according to claim 1 wherein said selected pressure is ranges between 0 and 2000 psi.

3. The high pressure liquid chromatography apparatus according to claim 1 wherein said incorporation reduces system volume.

4. The high pressure liquid chromatography apparatus according to claim 1 wherein said backflow preventer has a selected fixed resistance said selected fixed resistance ensuring that pulse dampeners within a chromatography system function efficiently with consistent performance of primary check valves of system pumps.

* * * * *